United States Patent [19]

Chevalier et al.

[11] Patent Number: 5,049,138
[45] Date of Patent: Sep. 17, 1991

[54] CATHETER WITH DISSOLVABLE TIP

[75] Inventors: Raymond P. Chevalier; Joseph J. Lacman, both of Bloomington, Ind.; John A. Hudson, Chelmsford, Mass.

[73] Assignee: Boston Scientific Corporation, Watertown, Mass.

[21] Appl. No.: 437,048

[22] Filed: Nov. 13, 1989

[51] Int. Cl.$^5$ ............................................. A61M 5/325
[52] U.S. Cl. ..................................... 604/265; 604/93
[58] Field of Search .................................. 604/52-53, 604/171-172, 264-266, 270, 93, 169, 280; 606/195

[56] References Cited

U.S. PATENT DOCUMENTS

| | | | |
|---|---|---|---|
| 3,780,740 | 12/1973 | Rhea | 604/270 |
| 4,692,152 | 9/1987 | Emde | 604/164 |
| 4,698,056 | 10/1987 | Ciannella | 604/164 |
| 4,790,310 | 12/1988 | Ginsburg et al. | 606/7 |
| 4,827,940 | 5/1989 | Mayer et al. | 128/642 |
| 4,876,126 | 10/1989 | Takemura et al. | 604/266 X |
| 4,936,835 | 6/1990 | Haaga | 604/265 |

*Primary Examiner*—C. Fred Rosenbaum
*Assistant Examiner*—Corrine Maglione

[57] ABSTRACT

The catheter of the present invention is adapted to be introduced into an internal organ in a body either percutaneously or through a body orifice for drainage of that organ where it can contact bodily fluids. The catheter includes a flexible tubular member that has an inner lumen and a rigid solid tip disposed at the end of the inner lumen. The tip is formed of a material that is slippery when wet, soluble in the bodily fluids and capable of absorbing radiographic fluids that are injected into inner lumen for identification of the location by X-rays. A narrow passageway is disposed in the tip and extends from the inner lumen to the distal end of the tip. The passageway is adapted to receive a guide wire for insertion of the catheter into an internal organ.

27 Claims, 1 Drawing Sheet

CATHETER WITH DISSOLVABLE TIP

BACKGROUND OF THE INVENTION

The present invention relates to a catheter that is to be placed into a body and may be guided into position on a guide wire into an organ for its drainage. Especially, the present invention relates to a catheter with an internal guiding passageway in a dissolvable tip so that when the catheter is in place in the organ, the tip will dissolve and allow drainage through the main lumen. In particular, the invention relates to a catheter with a tip that is slippery when wet, dissolvable in bodily fluids and has a composition which can absorb radiographic contrast liquids that are passed into it.

DESCRIPTION OF THE PRIOR ART

Many catheters are disclosed for insertion into organs of the body. To place the catheter in the correct location, the surgeon incises the body and inserts a guide wire (housed in a cannula) into the organ that is to be catheterized for drainage. The guide wire is temporarily anchored in the organ, the cannula is withdrawn, and the catheter is then advanced over the guide wire until it reaches the desired location in the organ. The guide wire is then withdrawn. The catheters of the prior art frequently have a blunt end and narrow opening formed therein. The opening is only slightly larger than the guide wire itself. Ports on the sidewalls of the catheter are relied on primarily for the drainage. The main lumen of the catheter itself, however, is not available for direct drainage because the body of the catheter is substantially sealed at the end since it only has an opening of a size that will receive the guide wire. Moreover, ultimate disposition of the catheter can be misjudged by the surgeon because of placement of the blunt ends of some of the catheters are not readily detectable through X-rays.

Catheters with soluble tips are known to the art. For example, the U.S. Pat. No. to Taylor, 3,736,939, discloses a balloon inflated retention type catheter that has an imperforate, water soluble catheter tip which fits around the open end of the catheter tube. The U.S. Pat. No. to Bried, 2,691,373, discloses a colon flushing nozzle with a dissolvable tip. In Bried, a dissolvable hollow shell tip is disclosed which has a central opening that is of substantially the same width as the nozzle in which it fits. The U.S. Pat. No. to McShirley, 2,603,217, discloses a dissolvable tip that has a sleeve which fits over the end of the catheter for introducing fluids into a patient's body. A catheter having a dissolvable tip with a balloon located near the tip and an auxiliary drainage opening on the side of the catheter tube is disclosed by Taylor, 3,736,939.

SUMMARY OF THE INVENTION

According to the present invention, the solid tip of the catheter is formed of a polymeric material that is slippery when wet and has a narrow central lumen so that the catheter may be easily advanced on the guide wire into the body, either percutaneously or through a body orifice, into the organ to be drained. Once there, the catheter tip will dissolve in the bodily fluids and eventually the entire lumen of the catheter will be available for drainage from the opening that is left when the tip dissolves. In many of the devices of the prior art, only ports that are disposed on the sidewalls of the tubular catheter were available for drainage. More efficient drainage is now available because the entire lumen is open to receive the bodily fluids that can be drained after the tip dissolves. Additionally, we have discovered that through the use of certain polymeric materials that are slippery when wet and dissolvable in bodily fluids, these materials can absorb radiographic contrast liquids to become opaque to X-rays. Because of such absorption, the surgeon can easily inject a radiographic contrast liquid into the tubular member and thence into the tip to identify the precise location of the tip during a procedure.

Preferably, the solid tip is formed of a water soluble polymer such as polyvinyl alcohol although alternatives are available such as polyethylene oxide, polyethylene glycol, polyacrylamides, polyvinyl pyrolidone, polyacrylic acid and the like. Such materials can be readily molded into a shape such as described herein.

The catheter includes a flexible tubular member having an inner lumen into which a portion of the tip fits. The tip is a solid unitary body. It has an external portion that is shaped in a generally conical configuration and an internal portion that has a generally cylindrical configuration, the cylindrical portion being disposed at the base of the cone. The internal portion is arranged to be disposed and rigidly held in the lumen. A narrow passageway is disposed axially through the tip and it extends from the mouth of the tip at the inner lumen of the tubular member to the distal end. The diameter of the passageway is substantially uniform from the mouth to the distal end. It is adapted to receive a guide wire for the insertion of the catheter into the internal organ and because of the fairly uniform diameter, the catheter will not tangle on the guide wire before it is seated in the organ.

DESCRIPTION OF THE PREFERRED EMBODIMENTS

Figure 1:
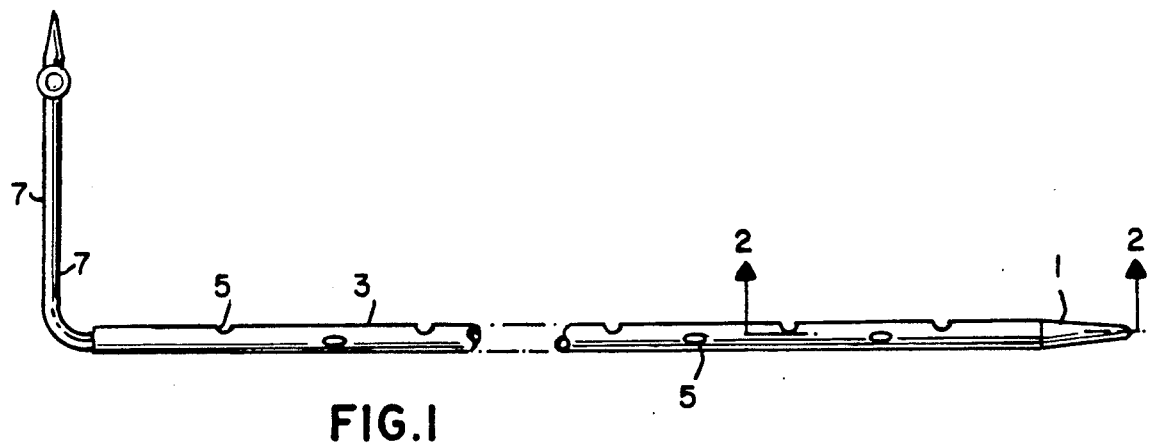
FIG. 1 is a side elevational view of a catheter and tip according to the present invention.

Referring now to FIG. 1, a catheter is shown which includes a flexible tubular member 3 formed of any of the polymeric materials conventionally used for catheters. The tubular member is biocompatible and inert to bodily fluids and optimally approaches a softness of body tissue so as to avoid irritation of tissues when the catheter is in place. Materials having such characteristics include urethane, silicone and materials sold under the tradename "C-Flex" (sold by Concept, Inc., of Clearwater FL) and PERCUFLEX (provided by Medi-Tech, Inc., of Watertown, MA).

The catheter preferably has an outer diameter of about 2.7 to 5.3 mm. and the inner lumen has a diameter of about 1.6 to 4.0 mm. It is flexible so as to be movable within the body in which it is inserted. Auxiliary drainage ports 5 having diameters of about 0.5 to 6 mm. are disposed in the wall of the catheter and communicate with the inner lumen. The auxiliary drainage ports 5 can be placed anywhere along the length of the catheter, as desired for effective drainage, as is well known in the art. In the embodiment that is shown, a suture 7 is attached to the catheter to facilitate its removal when the need requires. A portion of the tip 1 is disposed inside the lumen of the catheter 3.

Figure 2:
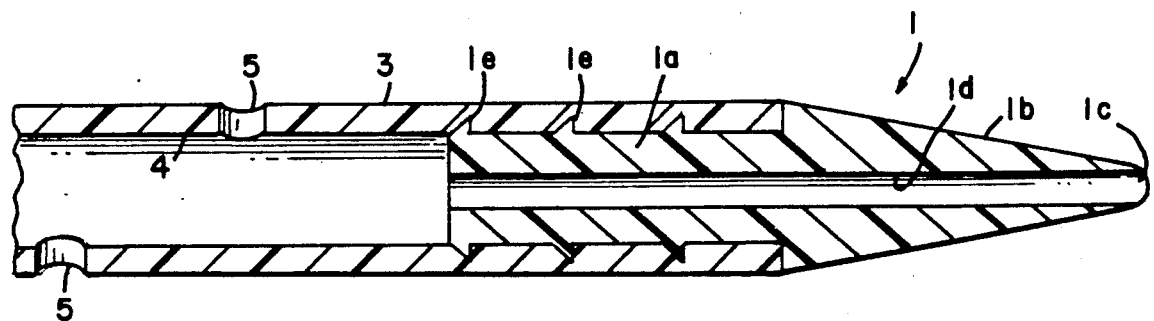
FIG. 2 is an enlarged cross-sectional view taken along the line 2—2 of FIG. 1 showing the catheter and tip with the tip disposed in the catheter.

Referring now to FIG. 2, the catheter tip 1 is shown disposed within the inner lumen 4 of the catheter 3. The tip 1 is formed of a unitary, stiff solid body of molded polymeric material and includes the inner portion 1a and an outer portion 1b. Outer portion 1b is formed in a generally conical shape with a rounded distal end 1c. As shown, the tip 1 has a series of annular rings 1e which extend outwardly from an inner portion 1a of the tip 1 so as to anchor the tip firmly within the inner lumen 4 of the catheter 3. While the tip 1 can be anchored into the lumen 4 of the catheter 3 by the rings as shown, heating and melting the tip and/or adhesives can also be used to accomplish the fastening. Inner portion 1a has a diameter substantially the same as the inner diameter of the inner lumen 4 and is about 1.6 to 4.0 mm. The base of the outer portion 1b has a diameter about 2.7 to 5.3 mm. and is substantially the same as the diameter of the tubular member 3. The tip is preferably formed of a polymeric material that has a hardness of about 30 Shore D—about 40 Rockwell M. The tensile strength is preferably between about 2,500 and 5,000 psi, an elongation between about 25% and 500%.

A narrow axial passageway 1d having an internal diameter of 0.45 to 1.27 mm. is disposed in the tip and communicates between the lumen 4 and, the distal end 1c. The internal diameter of the passageway 1d is just slightly greater than the diameter of the guide wire which will be threaded through it. The diameter is fairly uniform, although it can be slightly truncated to easily receive the wire.

After the catheter is placed into organ to be drained, the tip will dissolve at a predetermined rate and the entire inner lumen 4 of the catheter 3 will be available for drainage. Suitable materials for the tip 1 are those water soluble polymers set out previously. Preferably the water solubility is about 45 seconds on a 1.5 mil thick sample in 25° C., water under slight agitation. The slipperiness, based upon the coefficient of friction $\mu$ is between about 0.02 and 0.3, preferably 0.08 $\mu$.

These polymers may be used alone or in combination with water soluble non-toxic plasticizers, such as the various well known glycols or glycerols, to obtain the desired combination of rigidity and disintegration time. The polymers chosen preferably will disintegrate and dissolve substantially completely when immersed in aqueous fluid over a predetermined number of hours or days, the adjustment of which is well known in the art.

Through the use of a catheter of the present invention, not only can fluids be removed but also substantial amounts of cellular debris and disconnected fragmented tissue which has become dislodged can be removed. In the catheters that do not open to the full lumen, such materials do not easily pass through the openings 5 due to their small size. Such particles frequently tended to collect in or around the openings and impede the desired the drainage.

Quite surprisingly we have found that the polymeric materials that dissolve in bodily fluids can absorb radiographic contrast liquids that are injected into the catheter and ultimately into the passageway 1d. Since the tip 1 will absorb the radiographic contrast liquids, the tip itself will be rendered radioopaque until total dissolution is complete, thus rendering its location amenable to identification by X-ray.

Additionally we have found that the materials of the tip can be color coded in an array of colors by mixing non-toxic coloring agents into the polymeric blend to enable the user to easily identify catheters of different diameters or dissolution rates.

To make the catheter tip, we have found that the following procedure provides a device that is adequate for its use with the catheter tube.

The tip may be formed and is most preferred to be formed by conventional thermoplastic processing methods. One such method that is employed is injection molding. This process can be described as one that produces three dimensional parts through a discontinuous start and stop process. For example, polyvinyl alcohol may be used containing up to approximately 60% by weight propylene glycol. It is dried for a period of approximately four hours at 80° C. The material may then be processed in an injection molding machine at a melt temperature between 140° C. and 220° C., preferably 170° C. The part is then removed from the mold after it has cooled and then secured to the tubing.

It is apparent that modifications and changes can be made within the spirit and scope of the present invention. It is our intention, however, only to be limited by the scope of the appended claims.

As our invention, we claim:

1. A catheter to be introduced into an internal organ in a body either percutaneously or through a body orifice where it can contact bodily fluids, said catheter comprising:
    a flexible tubular member having an inner lumen;
    a rigid solid tip having an inner face and a distal end, said tip being disposed in said lumen, said tip being formed entirely of a molded polymeric material that is slippery when wet, soluble in said bodily fluids and able to absorb radiographic media injected into said tubular member whereby to render said tip radio-opaque;
    a narrow passageway disposed in said tip, said passageway extending from said inner face to the distal end of said tip, said passageway being adapted to receive a guide wire for the insertion of said catheter into an internal organ.

2. The catheter according to claim 1 wherein a portion of said tip is disposed inside of said inner lumen.

3. The catheter according to claim 1 wherein said tip is a unitary body and said passageway extends through said tip on its long axis, said tip having an external portion shaped in a generally conical configuration and an internal portion having a generally cylindrical configuration, said internal portion being arranged to be disposed in said lumen, said internal portion extending coaxially from the base of said external portion and being disposed within said tubular member.

4. The catheter according to claim 3 wherein the outer diameter of said internal portion has a diameter substantially the same as the internal diameter of said inner lumen.

5. The catheter according to claim 4 wherein the internal diameter of said inner lumen is between about 1.6 and 4.0 mm. and the outer diameter of said internal portion is between about 2.7 and 5.3 mm.

6. The catheter according to claim 3 wherein the outer diameter of the tubular member is substantially the same as the diameter of the base of the cone of said tip.

7. The catheter according to claim 3 wherein said fastening means are a series of annular rings disposed on said inner portion of said tip.

8. The catheter according to claim 3 wherein said fastening means includes adhesives.

9. The catheter according to claim 3 wherein the material is polyvinyl alcohol.

10. The catheter according to claim 9 wherein the diameter of said passageway is between about 0.45 and 1.27 mm.

11. The catheter according to claim 10 wherein a plurality of openings are formed on the sidewalls of said tubular member.

12. The catheter according to claim 1 further including fastening means connecting said tip to said inner lumen.

13. The catheter according to claim 1 wherein the tip is formed of a water soluble material selected from the group consisting of polyvinyl alcohol, polyethylene oxide, polyethylene glycol, polyacrylamides, polyvinyl pyrrolidone, polyacrylic acid and the like.

14. The catheter according to claim 1 wherein the diameter of said passageway is significantly less than the diameter of said inner lumen.

15. The catheter according to claim 14 wherein the passageway has a fairly uniform diameter from the inner face to the distal tip.

16. The catheter according to claim 1 wherein a plurality of additional openings are formed on the sidewalls of said tubular member.

17. The catheter according to claim 16 wherein said tip is color coded in a predetermined array of colors to designate the diameter of the catheter and/or the dissolution rate.

18. A catheter to be introduced into an internal organ in a body either percutaneously or through a body orifice where it can contact bodily fluids, said catheter comprising:

a flexible tubular member having an inner lumen;

a rigid solid tip having an inner face and a distal end, said tip being disposed at said lumen, said tip being formed entirely of a molded polymeric material that is slippery when wet, soluble in said bodily fluids and able to absorb radiographic media injected into said tubular member whereby to render said tip radio-opaque, said tip being a unitary body, said tip having an external portion shaped in a generally conical configuration and an internal portion having a generally cylindrical configuration, said internal portion being arranged to be disposed in said lumen, said internal portion extending coaxially from the base of said external portion and being disposed within said tubular member;

a narrow passageway disposed in said tip, said passageway extending from said inner face to the distal end of said tip, said passageway adaptable to receive a guide wire for the insertion of said catheter into an internal organ.

19. The catheter according to claim 18 wherein the outer diameter of said internal portion has a diameter substantially the same as the internal diameter of said inner lumen.

20. The catheter according to claim 19 wherein the internal diameter of said inner lumen is between about 1.6 and 4.0 mm. and the outer diameter of said internal portion is between about 2.7 and 5.3 mm.

21. The catheter according to claim 19 wherein the outer diameter of the tubular member is substantially the same as the diameter of the base of the cone of said tip.

22. The catheter according to claim 18 further including fastening means connecting said tip to said inner lumen.

23. The catheter according to claim 22 wherein said fastening means are a series of annular rings disposed on said inner portion of said tip.

24. The catheter according to claim 18 wherein the tip is formed of a water soluble material selected from the group consisting of polyvinyl alcohol, polyethylene oxide, polyethylene glycol, polyacrylamides, polyvinyl pyrrolidone, polyacrylic acid and the like.

25. The catheter according to claim 24 wherein the material is polyvinyl alcohol.

26. The catheter according to claim 18 wherein the diameter of said passageway is significantly less than the diameter of said inner lumen.

27. The catheter according to claim 26 wherein a plurality of additional openings are formed on the sidewalls of said tubular member.

* * * * *